United States Patent [19]

Hermans

[11] Patent Number: 4,953,633

[45] Date of Patent: Sep. 4, 1990

[54] APPARATUS FOR KEEPING AT A DETERMINED TEMPERATURE A PRODUCT MIXTURE CONSISTING OF A LIQUID CONTAINING SOLID PIECES

[75] Inventor: Willem F. Hermans, Amstelveen, Netherlands

[73] Assignee: Stork Amsterdam B.V., Amsterdam, Netherlands

[21] Appl. No.: 430,817

[22] Filed: Nov. 2, 1989

[30] Foreign Application Priority Data

Nov. 3, 1988 [NL] Netherlands ............ 8802697

[51] Int. Cl.⁵ ............................................. F28F 13/12
[52] U.S. Cl. ................... 165/109.1; 165/120; 366/149; 366/303
[58] Field of Search ........... 165/109.1, 94, 120; 366/149, 303; 415/71; 416/176, 223 R, 231 A

[56] References Cited

U.S. PATENT DOCUMENTS

| 915,139 | 3/1909 | Werner | 366/303 |
|---|---|---|---|
| 1,870,980 | 8/1932 | Altwegg | 366/303 X |
| 2,304,579 | 12/1942 | Lindsey | 62/114 |
| 2,663,623 | 12/1953 | Anderson | 23/270 |
| 3,709,664 | 1/1973 | Krekeler et al. | 23/285 |
| 3,788,609 | 1/1974 | Toczyski | 259/5 |
| 4,154,798 | 5/1979 | Bittner | 422/162 |
| 4,334,788 | 6/1982 | Miner | 366/303 |

FOREIGN PATENT DOCUMENTS 1095966 6/1955 France .
8601221 12/1987 Netherlands .
788757 1/1958 United Kingdom .

Primary Examiner—John Rivell
Assistant Examiner—Allen J. Flanigan
Attorney, Agent, or Firm—Weintraub, DuRoss & Brady

[57] ABSTRACT

An apparatus comprises a cylindrical vessel provided at one end with an inlet and at the other end with an outlet for the mixture. A conveyor mechanism acting selectively on the solid pieces in the mixture is disposed in the vessel. The conveyor mechanism has a rotor in the form of a shaft coaxially rotatable in the vessel and provided with at least one series of rotor arms on the shaft, extending radially and lying substantially next to one another and spaced apart in the axial direction. The conveyor mechanism also has a stator in the form of at least one series of stator arms extending radially inwards from the wall of the vessel and lying substantially next to one another and spaced apart in the axial direction. The stator arms extend between the rotor arms and reach to a point close to the rotor shaft. The mutual distance between the rotor arms and the mutual distance between the stator arms, in the axial direction, varies from the inlet to the outlet, the variation occurring mainly in one direction. In the case both of the rotor arms and of the stator arms a radially extending side edge of an arm is, viewed in the axial direction of the rotor and the stator, adjacent to or situated within the periphery of a following arm, so that a solid piece moving through the vessel can pass through between two neighbouring arms only transversely to the axial direction of the vessel.

11 Claims, 4 Drawing Sheets

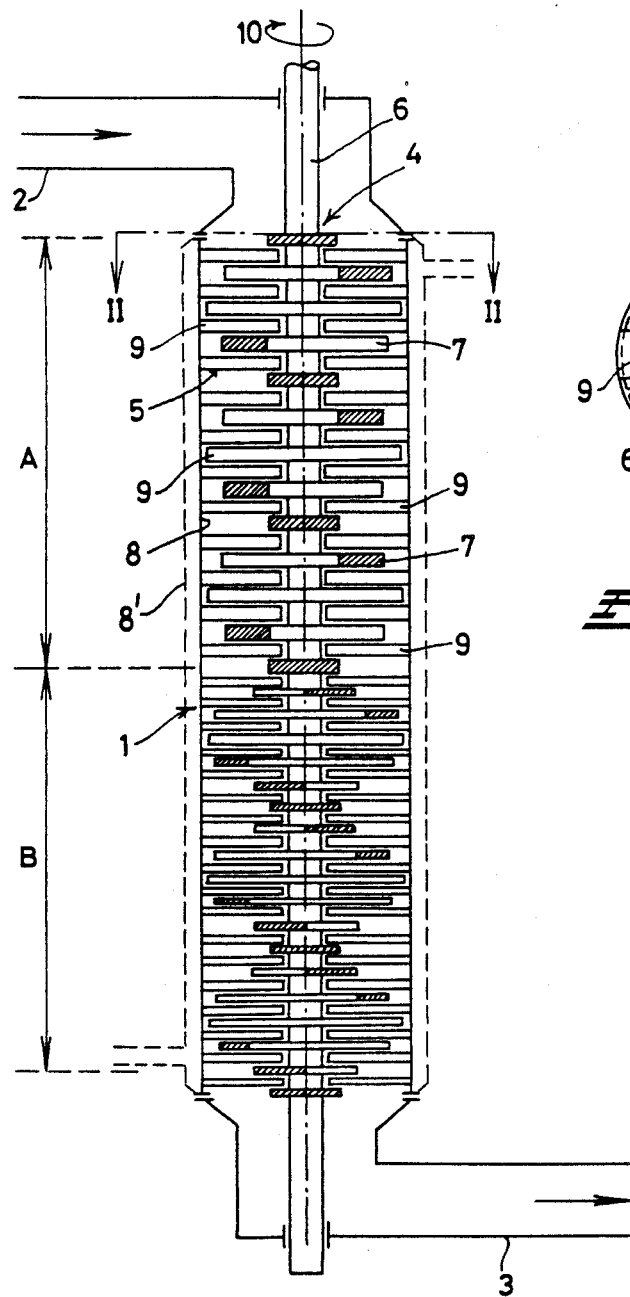
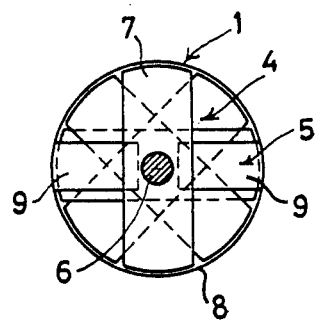
Fig. 1.
Fig. 2.

APPARATUS FOR KEEPING AT A DETERMINED TEMPERATURE A PRODUCT MIXTURE CONSISTING OF A LIQUID CONTAINING SOLID PIECES

BACKGROUND OF THE INVENTION

The invention relates to an apparatus for keeping at a determined temperature, for a determined time, a product mixture flowing therethrough and consisting of a liquid of low to medium viscosity containing solid pieces, which comprises a cylindrical vessel provided at one end with an inlet and at the other end with an outlet for the mixture, a conveyor mechanism acting selectively on the solid pieces in the mixture being disposed in the vessel, whereby the speed at which the solid pieces are conveyed through the vessel can be adjusted irrespective of the rate of flow of the liquid through the vessel, said conveyor mechanism having a rotor in the form of a shaft coaxially rotatable in the vessel and provided with at least one series of rotor arms mounted on the shaft, extending radially and lying substantially next to one another and spaced apart in the axial direction, the ends of said arms reaching to a point close to the inner wall of the vessel, and also having a stator in the form of at least one series of stator arms extending radially inwards from the wall of the vessel and lying substantially next to one another and spaced apart in the axial direction, said stator arms extending between the rotor arms and reaching to a point close to the rotor shaft.

In the "through flow" heating or cooling by a heat exchanger (for example a tubular heat exchanger) of liquids of low to medium viscosity contain a certain volume percentage of solid pieces (for example soup containing pieces of vegetables and meat), heat transfer takes place from the wall of the heat exchanger through the conveyor liquid, the flow of which may or may not be turbulent, to the outside of the solid pieces and thence to the core of these pieces. With this kind of heat transfer the conveyor liquid will have reached the desired end temperature more quickly than the core of the solid pieces entrained by the liquid. To enable the core of the solid pieces also to attain the same temperature as the liquid, the mixture is passed through the above-mentioned apparatus and the solid pieces are retained for determined time by a conveyor mechanism disposed in the vessel, while the liquid can flow through unhindered. The time during which the solid pieces are retained is so selected that the core of the solid pieces being heated or cooled by the liquid flowing over them will also have reached the required temperature. It may then occur inter alia that during the heating of the mixture the liquid will remain too long at the desired end temperature, so that the quality of the liquid is impaired.

In an apparatus known from Netherlands Patent Specification No. 8601221 the rotor arms are mounted in the form of a screw on the rotor shaft. The stator arms lie one behind the other, viewed in the axial direction. The mutual distance between the rotor arms and the stator arms is the same over the entire length of the apparatus.

The known apparatus has the shortcoming that it can retain only solid pieces whose measurements are above a certain value. If the mixture contains solid pieces of different dimensions, each requiring a different residence time in an apparatus of this kind, a plurality of the above described apparatuses, disposed serially, will be needed so that the cost of an installation equipped with these apparatuses is increased.

SUMMARY OF THE INVENTION

The object of the invention is to provide an apparatus of the above described type which is adapted to retain solid pieces of different dimensions, in such a manner that the residence time of the solid pieces in the apparatus is adjusted to the dimensions of these solid pieces.

This object is attained by an apparatus of the above described type wherein the mutual distance between the rotor arms, in the axial direction, varies from the inlet to the outlet, the variation occurring mainly in one direction, while in the case both of the rotor arms and of the stator arms a radially extending side edge of an arm is, viewed in the axial direction of the rotor and the stator, adjacent to or situated within the periphery of a following arm, so that a solid piece moving through the vessel can pass through between two neighbouring arms only transversely to the axial direction of the vessel.

With an apparatus according to the invention it is possible, in one and the same apparatus for the residence time of the solid pieces in a mixture to be adjusted in dependence on the dimensions of the solid pieces. Smaller solid pieces will be able to flow unhindered through the first part of the conveyor mechanism and will be retained only in a last part of the conveyor mechanism and conveyed onwards by the conveyor mechanism, while the larger pieces will be retained at an earlier stage. The residence time of the smaller pieces in the apparatus is therefore shorter than that of the larger pieces. Correct selection of the distance between the rotor arms and the stator arms enables the optimum residence time to be adjusted for each of the solid pieces, while the residence time in the apparatus which is desired for the liquid is determined by the free capacity of the vessel and the rate of flow of the liquid.

The distance between the arms can be so selected that the mutual distance between the arms in a determined region of the length of the rotor and stator respectively is the same, while the mutual distance between the arms varies for the various regions from the inlet to the outlet. The solid pieces are thus retained, and conveyed onwards by the conveyor mechanism, in fractions according to size.

It is, however, also possible for the mutual distance between the arms to vary continuously from the inlet to the outlet. This results in what may be called a continuous sorting of the solid pieces in accordance with size, so that each solid piece substantially has a residence time in the apparatus adjusted to its dimensions.

Further features and advantages of the apparatus according to the invention will emerge from the following description of one example of embodiment, given with reference to the drawings.

BRIEF DESCRIPTION OF THE DRAWINGS

FIG. 1 shows very schematically a determined form of construction of the apparatus according to the invention;

FIG. 2 is a view on the line II—II in FIG. 1;

DETAILED DESCRIPTION OF A PREFERRED EMBODIMENT

Figure 3:
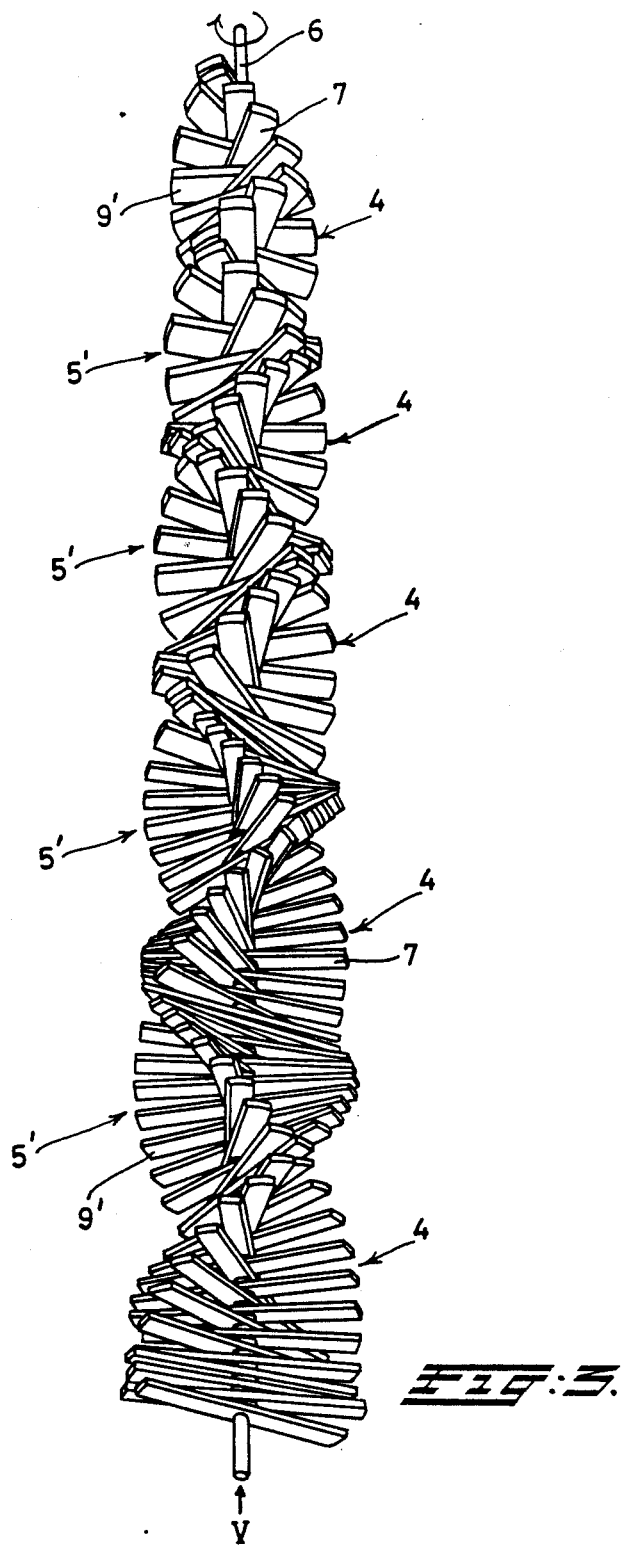
FIG. 3 is a view in perspective of a conveyor mechanism in another form of construction of the apparatus according to the invention.

FIGS. 1 and 2 show very schematically a determined form of construction of an apparatus for keeping at a determined temperature, for a determined time, a product mixture consisting of a liquid of low to medium viscosity containing solid pieces which flows therethrough. The apparatus comprises a cylindrical vessel 1, which at one end is provided with an inlet 2 and at the other end with an outlet 3 for the mixture. In the vessel 1 is disposed a conveyor mechanism which acts selectively on the solid pieces in the mixture, and which enables the residence time of the solid pieces n the vessel 1 to be adjusted irrespective of the rate of flow of the liquid through the vessel. The conveyor mechanism consists of a rotor 4 and a stator 5. The rotor 4 consists of a shaft 6 coaxially rotatable in the vessel 1 and provided with a series of rotor arms 7 extending radially and spaced apart in the axial direction. The rotor arms 7 are disposed on the shaft 6 in the form of a screw. The ends of the rotor arms 7 extend to a point close to the inside wall 8 of the vessel 1. The stator 5 consists of a series of stator arms 9 extending radially inwards from the wall 8 of the vessel 1 and spaced apart in the axial direction. The stator arms 9 lie between the rotor arms 7 and extend to a point close to the rotor shaft 6. In the form of construction of the apparatus illustrated in FIGS. 1 and 2 the stator arms lie in two straight rows in the longitudinal direction of the apparatus, these rows lying diametrically opposite each other. It is also possible to provide only one row or more than two rows of stator arms.

In the vessel the conveyor mechanism forms compartments which are bounded by the wall 8 of the vessel 1, the arms 7 of the rotor 4 and the arms 9 of the stator 5. The walls of these compartments are permeable to liquid and to solid pieces which are so small that they can move through between the arms. Solid pieces which are so large that they cannot pass through between the arms remain confined in a compartment. Through the rotation of the rotor formed by the shaft 6 and the arms 7 in the direction of the arrow 10 in FIG. 1, the compartments move, as it were, from top to bottom through the vessel 1, and therefore from the inlet 2 in the direction of the outlet 3. The speed at which solid pieces contained in a compartment are conveyed through the vessel is thus determined by the speed of rotation of the rotor 4. The speed at which solid pieces confined in a compartment are conveyed is therefore independent of the rate of flow of the liquid containing the smallest solid pieces which can pass through between the arms.

In the apparatus illustrated in FIGS. 1 and 2 the mutual distance between the rotor arms 7 and the mutual distance between the stator arms 9 in the axial direction increases from the inlet 2 to the outlet 3. In addition, the rotor arms 7 and the stator arms 9 are so disposed that in the case both of the rotor arms and of the stator arms a radially extending side edge of an arm is, viewed in the axial direction of the rotor 4 and the stator 5, adjacent to or situated within the periphery of a following arm (see FIG. 2). A solid piece moving through the vessel 1 can therefore pass through between two neighbouring arms only transversely to the axial direction of the vessel.

The mutual distance between the rotor arms 7 and the stator arms 9 is greater in the part A of the apparatus which adjoins the inlet 2 than in the part B of the apparatus following the part A and adjoining the outlet 3. It is thus possible to bring about a separation between solid pieces in a mixture of liquid and solid pieces passing through the apparatus. Solid pieces which are so small that they can pass through between the arms of the part B of the apparatus flow through the vessel together with the liquid Solid pieces which have dimensions such that theY can pass through between the arms of the part A, but not between the arms of the part B, are caught in the compartments formed in the part B by the rotor arms 7 and the stator arms 9 and, through the rotation of the rotor 4, are conveyed onwards in the direction of the outlet 3. Solid pieces whose dimensions are such that they cannot pass through between the arms of the part A are caught in the compartments formed in the part A by the rotor arms 7 and the stator arms 9 and, through the rotation of the rotor, are conveyed onwards through the vessel in the direction of the outlet 3. This has the consequence that the residence time in the vessel in the case of solid pieces which are caught in the part A of the vessel is longer than the residence time in the vessel in the case of the smaller solid pieces which are caught in the part B of the vessel, while the residence time of the smallest solid pieces, which pass through between the arms together with the liquid, is equal to the residence time of the liquid in the vessel.

It is also possible for the conveyor mechanism to be so constructed that the distance between the arms 7 and 9 respectively of the rotor 4 and the stator 5 respectively decreases continuously from the inlet 2 to the outlet 3. A continuous sorting in respect of size of the solid pieces will thus be achieved, in contrast to multiple sorting into a limited number of fractions according to size, such as is achieved with the form of construction shown in FIG. 1.

In FIG. 3 a conveyor mechanism of another form of construction of the apparatus according to the invention is illustrated In this form of construction the arms 9' of the stator 5', like the arms 7 of the rotor 4, are disposed in the form of a screw. The pitch of the screw in which the arms 9' of the stator 5' are disposed is equal, in FIG. 3, to the pitch of the screw in which the arms 7 of the rotor 4 are disposed, while the threads of the screw of the stator 5' and the rotor 4 turn in opposite directions about the centre line of the stator or the rotor respectively.

In FIG. 3 the compartments bounded by the arms 7 and 9' of the rotor 4 and the stator 5' respectively can also be clearly seen. By mounting the arms of the stator as well as the arms of the rotor in the form of a screw, with the screw threads of the stator and the rotor turning in opposite directions about their centre lines, relatively short compartments are obtained, so that the total length of the apparatus according to the invention can be restricted.

The pitch of the screw in which the stator arms 9' are disposed can also be different from the pitch of the screw in which the rotor arms 7 are disposed It is also conceivable for the screw threads of the stator and the rotor to turn in the same direction about their centre lines. In that case the arms 9' and 7 must be disposed with different pitches on the stator 5' and the rotor 4 respectively, since otherwise compartments will not be formed.

It may be observed that the arms 9' of the stator 5' the conveyor mechanism shown in FIG. 3 are fastened at their ends to the wall 8 of the vessel 1, and that the shaft 6 of the rotor 4 is free to rotate relative to the stator arms 9'.

Figure 4:
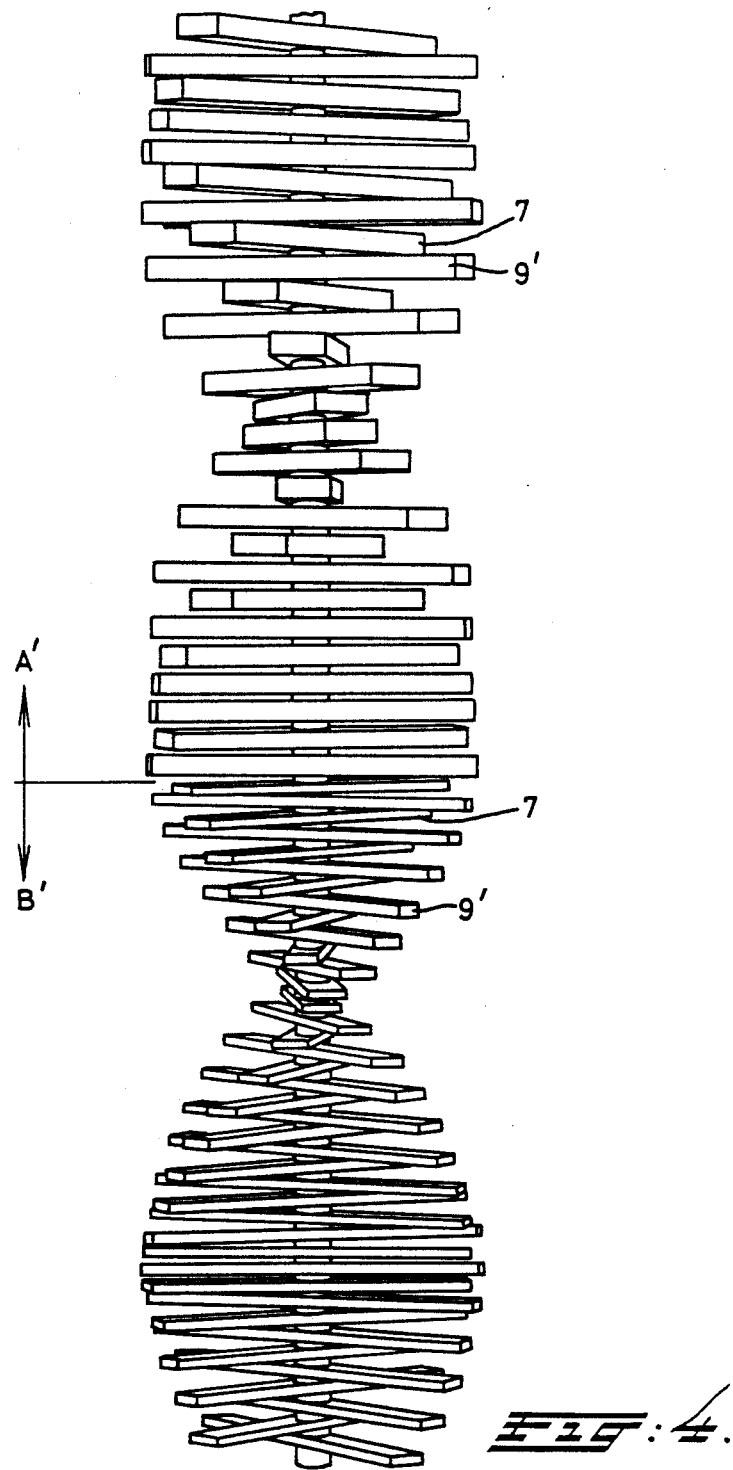
FIG. 4 is a side view on a larger scale of a part of the conveyor mechanism shown in FIG. 3.

FIG. 4 shows on a larger scale and in side view a part of the conveyor mechanism shown in FIG. 3. In FIG. 4 the transition from a part A' to a part B' is clearly to be seen, the mutual distance between the rotor arms 7 and the mutual distance between the stator arms 9' being greater in the part A' than in the part B'.

Figure 5:
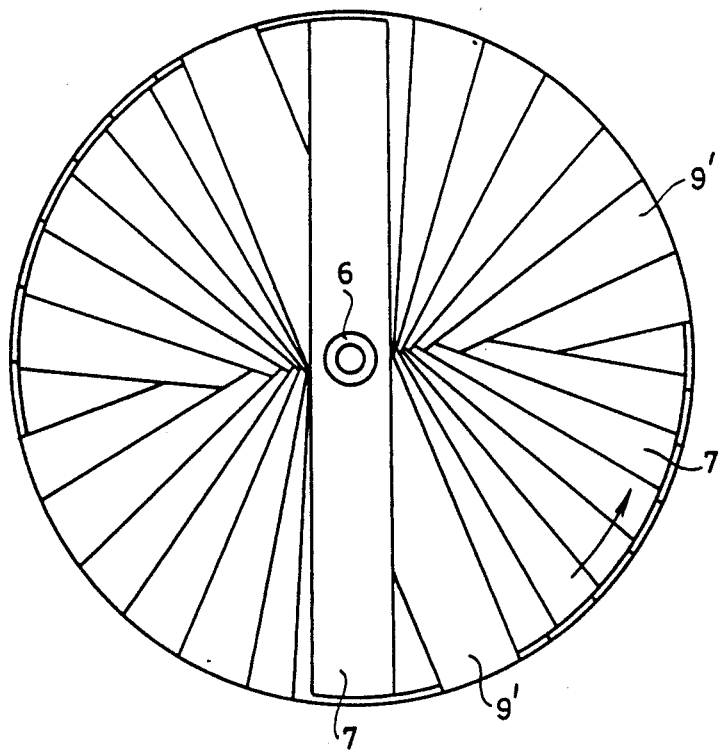
FIG. 5 is an end view in the axial direction, on a larger scale, of the conveyor mechanism shown in FIG. 3.

In FIG. 5 it can be seen that the rotor arms 7 and also the stator arms 9' partly overlap, viewed in the axial direction. It can thereby be ensured that a solid piece moving through the vessel can pass through between two neighbouring arms only transversely to the axial direction of the vessel, so that the mutual distance between the arms determines whether or not a solid piece will be allowed through. In FIG. 5 it can also be clearly seen that in a plane at right angles to the axis of the conveyor mechanism two rotor arms 7 or two stator arms 9 lie opposite and in line with one another.

In order to ensure the most regular possible outflow of solid pieces, the arms 7 of the rotor 4 and the arms 9' of the stator 5' can be disposed in a plurality of screw threads on the rotor shaft 6 and the wall 8 of the vessel 1 respectively, the number of screw threads of the rotor being different from that of the stator. Thus, for example, the stator may comprise three screw threads and the rotor two screw threads. If the number of screw threads of the rotor is equal to that of the stator, the compartments at the outlet end will all open at the same time, so that at that moment a large quantity of solid pieces will be freed. If the number of screw threads of the rotor is different from that of the stator, the compartments will open one after the other and the solid pieces in the compartments will also be released one after the other.

In both the above described forms of construction of the apparatus according to the invention the axial dimension of each rotor arm 7 is preferably approximately equal to and, in particular, slightly smaller than the axial distance between the two stator arms 9 and 9, respectively where the rotor arm 7 in question moves therebetween. The rotor arms then move as closely as possible along the stator arms, so that it is ensured that no deposition (for example of denatured albumen) can occur between the arms, whereby the mutual distance between the arms, and therefore the sieve characteristic, could be changed.

Inside the apparatus an equalization of temperatures takes place between the liquid, which flows into the apparatus at a determined temperature, and the solid pieces, the core of which has not yet reached the temperature of the liquid and whose mean temperature is thus different from that of the liquid flowing through. In order to prevent the liquid from undergoing too great a temperature change in passing through the apparatus, the vessel may be provided with a double wall, while between the two walls a closed space is formed which can be connected to pipe supplying a heating medium, for example steam, or a cooling medium if the mixture is to be cooled. A double wall of this kind, comprising an inner wall 8 and an outer wall 8', is indicated in FIG. 1, the outer wall 8' being shown in broken lines.

The apparatus according to the invention is preferably disposed vertically. The direction of flow is preferably selected in dependence on the difference in relative density between the carrier liquid and the solid pieces. If the relative density of the solid pieces is higher than that of the carrier liquid, the flow through the apparatus will preferably be from top to bottom. If the relative density of the solid pieces is lower than that of the carrier liquid, the flow will preferably be from bottom to top, and therefore oppositely to the direction of the force of gravity. This will ensure that the solid pieces will be situated in the downstream part of a compartment and therefore will not be subjected to the cutting or clipping action of the rotor arms 7 and the stator arms 9 or 9' at the upstream boundary of a compartment.

In the above described example of construction of the apparatus according to the invention the mutual distance between the rotor arms 7 and the stator arms 9, 9' decreases from the inlet 2 towards the outlet 3, as is preferable. In this case the largest pieces are caught in the first compartments at the inlet end of the vessel 1, and the smaller pieces further on in the vessel. In principle, the distance between the arms may also increase from the inlet 2 towards the outlet 3. In this case, however, the first compartments will retain all the solid pieces, while the smaller pieces, followed by the larger pieces, will be gradually "flushed out" into the following compartments. The sifting load will then be greater than when the large solid pieces are first retained and the smaller solid pieces can flow freely through the first part of the vessel.

Depending on the proportion by volume of the larger solid pieces, the first compartments (for the largest solid pieces) can be made smaller, for example by means of a smaller pitch of the screw threads in which the arms are arranged and/or of a smaller diameter of the vessel at that point.

The apparatus according to the invention can be used in an installation for continuous-flow heat treatment of a product mixture consisting of a liquid containing solid pieces. An installation of this kind is described in Dutch Patent Application No. 87 02819 (which does not constitute a prior publication) in the name of the Applicant. The apparatus according to the invention can then be used instead of the temperature maintenance apparatus included in that installation.

What is claimed is:

1. Apparatus for keeping at a determined temperature, for a determined time, a product mixture flowing therethrough and consisting of a liquid of low to medium viscosity containing solid pieces, which comprises a cylindrical vessel provided at one end with an inlet and at the other end with an outlet for the mixture, a conveyor mechanism acting selectively on the solid pieces in the mixture being disposed in the vessel, whereby the speed at which the solid pieces are conveyed through the vessel can be adjusted irrespective of the rate of flow of the liquid through the vessel, said conveyor mechanism having a rotor in the form of a shaft coaxially rotatable in the vessel and provided with at least one series of rotor arms on the shaft, extending radially and lying substantially next to one another and spaced apart in the axial direction, the ends of said arms reaching to a point close to the inner wall of the vessel, and also having a stator in the form of at least one series of stator arms extending radially inwards from the wall of the vessel and lying substantially next to one another and spaced apart in the axial direction, said stator arms extending between the rotor arms and reaching to a point close to the rotor shaft, and the mutual distance between the rotor arms and the mutual distance between the stator arms, in the axial direction, varying from the inlet to the outlet, the variation occurring mainly in one direction, while in the case both of the rotor arms and of the stator arms a radially extending side edge of an arm is, viewed in the axial direction of the rotor and the stator, adjacent to or situated within the periphery of a following arm, so that a solid piece moving through the vessel can pass through between two neighbouring arms only transversely to the axial direction of the vessel.

2. The apparatus of claim 1, wherein the mutual distance between the arms is constant in a determined region of the length of the rotor and stator respectively, while the mutual distance between the arms varies for each region from the inlet to the outlet.

3. The apparatus of claim 1, wherein the mutual distance between the arms varies continuously from the inlet to the outlet.

4. The apparatus of claim 1, wherein the mutual distance between the arms decreases from the inlet to the outlet.

5. The apparatus of claim 1, wherein the axial dimension of each rotor arm is approximately equal to and in particular somewhat smaller than the axial distance between the two stator arms where the rotor arm in question moves therebetween.

6. The apparatus of claim 1, wherein the arms of the rotor and the arms of the stator are disposed in the form of a screw on the rotor shaft and on the wall of the vessel respectively, the shape of the screw in which the arms are arranged differing from that of the screw in which the arms of the rotor are arranged.

7. The apparatus of claim 6, wherein the pitch of the screw in which the arms of the stator are arranged differs from the pitch of the screw in which the arms of the rotor are arranged.

8. The apparatus of claim 6, wherein the pitch of the screw in which the arms of the stator are arranged is equal to the pitch of the screw in which the arms of the rotor are arranged, while the screw threads of the stator and the rotor turn in opposite directions about the centre line of the stator and the rotor respectively.

9. The apparatus of claim 6, wherein the arms of the rotor and the arms of the stator are arranged in a plurality of screw threads on the rotor shaft and the wall of the vessel respectively, the number of screw threads of the rotor differing from that of the stator.

10. The apparatus of claim 1, wherein the wall of the vessel is a double wall.

11. An installation for the continuous-flow heat treatment of a product mixture consisting of a liquid containing solid pieces, which is equipped with an apparatus for keeping at a determined temperature, for a determined time, a product mixture flowing therethrough and consisting of a liquid of low to medium viscosity containing solid pieces, which comprises a cylindrical vessel provided at one end with an inlet and at the other end with an outlet for the mixture, a conveyor mechanism acting selectively on the solid pieces in the mixture being disposed in the vessel, whereby the speed at which the solid pieces are conveyed through the vessel can be adjusted irrespective of the rate of flow of the liquid through the vessel, said conveyor mechanism having a rotor in the form of a shaft coaxially rotatable in the vessel and provided with at least one series of rotor arms on the shaft, extending radially and lying substantially next to one another and spaced apart in the axial direction, the ends of said arms reaching to a point close to the inner wall of the vessel, and also having a stator in the form of at least one series of stator arms extending radially inwards from the wall of the vessel and lying substantially next to one another and spaced apart in the axial direction, said stator arms extending between the rotor arms and reaching to a point close to the rotor shaft, and the mutual distance between the rotor arms and the mutual distance between the stator arms, in the axial direction, varying from the inlet to the outlet, the variation occurring mainly in one direction, while in the case both of the rotor arms and of the stator arms a radially extending side edge of an arm is, viewed in the axial direction of the rotor and the stator, adjacent to or situated within the periphery of a following arm, so that a solid piece moving through the vessel can pass through between two neighbouring arms only transversely to the axial direction of the vessel.

* * * * *